United States Patent
Yoon et al.

(10) Patent No.: US 11,186,668 B2
(45) Date of Patent: Nov. 30, 2021

(54) PREPARATION METHOD FOR SUPER ABSORBENT POLYMER SHEET

(71) Applicant: LG Chem, Ltd., Seoul (KR)

(72) Inventors: Kiyoul Yoon, Daejeon (KR); Gicheul Kim, Daejeon (KR); Hyeon Choi, Daejeon (KR); Seongkyun Kang, Daejeon (KR); Ju Eun Kim, Daejeon (KR)

(73) Assignee: LG Chem, Ltd.

( * ) Notice: Subject to any disclaimer, the term of this patent is extended or adjusted under 35 U.S.C. 154(b) by 50 days.

(21) Appl. No.: 16/756,360

(22) PCT Filed: Apr. 30, 2019

(86) PCT No.: PCT/KR2019/005222
§ 371 (c)(1),
(2) Date: Apr. 15, 2020

(87) PCT Pub. No.: WO2019/216591
PCT Pub. Date: Nov. 14, 2019

(65) Prior Publication Data
US 2021/0079141 A1      Mar. 18, 2021

(30) Foreign Application Priority Data
May 11, 2018   (KR) .................. 10-2018-0054364
Apr. 29, 2019   (KR) .................. 10-2019-0049877

(51) Int. Cl.
*C08J 9/28*        (2006.01)
*C08F 220/06*   (2006.01)

(52) U.S. Cl.
CPC .............. *C08F 220/06* (2013.01); *C08J 9/28* (2013.01); *C08J 2201/0504* (2013.01); *C08J 2205/022* (2013.01); *C08J 2333/02* (2013.01)

(58) Field of Classification Search
CPC ......... C08F 220/06; C08F 220/28; C08J 9/28; C08J 2201/0504; C08J 2205/022;
(Continued)

(56) References Cited

U.S. PATENT DOCUMENTS 5,985,944 A    11/1999   Ishizaki et al.
6,100,305 A    8/2000    Miyake et al.
(Continued)

FOREIGN PATENT DOCUMENTS

EP    1966257 A2    9/2008
EP    2244747 A2    11/2010
(Continued)

OTHER PUBLICATIONS

European Search Report for Application No. EP19800809, dated Nov. 30, 2020, 8 pages.
(Continued)

*Primary Examiner* — Kara B Boyle
(74) *Attorney, Agent, or Firm* — Lerner, David, Littenberg,Krumholz & Mentlik, LLP

(57) ABSTRACT

A method of preparing a superabsorbent polymer sheet by polymerization of monomers in the presence of an encapsulated foaming agent and an inorganic foaming agent is provided. According to the method of preparing the superabsorbent polymer sheet of the present invention, a porous and flexible superabsorbent polymer sheet may be prepared.

13 Claims, 1 Drawing Sheet

(58) Field of Classification Search
CPC .............. C08J 2333/02; C08J 2207/12; C08J 2205/02; C08J 2203/02; C08J 9/32; C08J 2333/00; C08J 2203/22; C08J 9/08; A61L 15/60

See application file for complete search history.

(56) References Cited

U.S. PATENT DOCUMENTS

| | | |
|---|---|---|
| 7,163,966 B2 | 1/2007 | Joy et al. |
| 8,198,385 B2 | 6/2012 | Gartner et al. |
| 8,252,873 B1 | 8/2012 | Gartner et al. |
| 9,737,874 B2 | 8/2017 | Wattebled et al. |
| 10,391,195 B2 | 8/2019 | Henn et al. |
| 2005/0137546 A1 | 6/2005 | Joy et al. |
| 2007/0129517 A1 | 6/2007 | Lang et al. |
| 2009/0191408 A1 | 7/2009 | Tian et al. |
| 2009/0192481 A1 | 7/2009 | Dodge, II et al. |
| 2009/0239966 A1 | 9/2009 | Matsumoto et al. |
| 2012/0001122 A1 | 1/2012 | Wattebled et al. |
| 2013/0096000 A1 | 4/2013 | Tian et al. |
| 2014/0054497 A1 | 2/2014 | Wattebled et al. |
| 2014/0257223 A1 | 9/2014 | Henn et al. |
| 2016/0096944 A1 | 4/2016 | Wattebled et al. |
| 2016/0354757 A1 | 12/2016 | Lee et al. |
| 2018/0178193 A1 | 6/2018 | Lee et al. |

FOREIGN PATENT DOCUMENTS

| | | | | |
|---|---|---|---|---|
| EP | 3248991 A1 | 11/2017 | | |
| EP | 3636698 A1 | 4/2020 | | |
| JP | H10119042 A | 5/1998 | | |
| JP | H11349687 A | 12/1999 | | |
| JP | 2007514833 A | 6/2007 | | |
| JP | 2007314794 A | 12/2007 | | |
| JP | 2012522880 A | 9/2012 | | |
| JP | 5336704 B2 | 11/2013 | | |
| JP | 2014533530 A | 12/2014 | | |
| KR | 20070094741 A | 9/2007 | | |
| KR | 20080091764 A | 10/2008 | | |
| KR | 20080091764 A | * 10/2008 | ............ | C08F 220/06 |
| KR | 20120043165 A | * 5/2012 | ................ | C08J 9/32 |
| KR | 20120043165 A | 5/2012 | | |
| KR | 20160056326 A | 5/2016 | | |
| KR | 101635257 B1 | 6/2016 | | |
| KR | 20160063956 A | * 6/2016 | ................ | C08J 9/08 |
| KR | 20160063956 A | 6/2016 | | |
| KR | 101650261 B1 | 8/2016 | | |
| KR | 101786285 B1 | 10/2017 | | |
| KR | 101789350 B1 | 10/2017 | | |
| WO | 1996017884 A1 | 6/1996 | | |
| WO | 2005063313 A1 | 7/2005 | | |
| WO | 2019050183 A1 | 3/2019 | | |
| WO | 2019216591 A1 | 11/2019 | | |
| WO | 2019216592 A1 | 11/2019 | | |
| WO | 2020067662 A1 | 4/2020 | | |

OTHER PUBLICATIONS

George Odian, "Principles of Polymerization", Second Edition, A Wiley-Interscience Publication, 1981, p. 203.

International Search Report for Application No. PCT/KR2019/005222 dated Aug. 9, 2019.

Reinhold Schwalm, UV Coatings: Basics, Recent Developments and New Application, Elsevier, Dec. 21, 2006, p. 115.

* cited by examiner

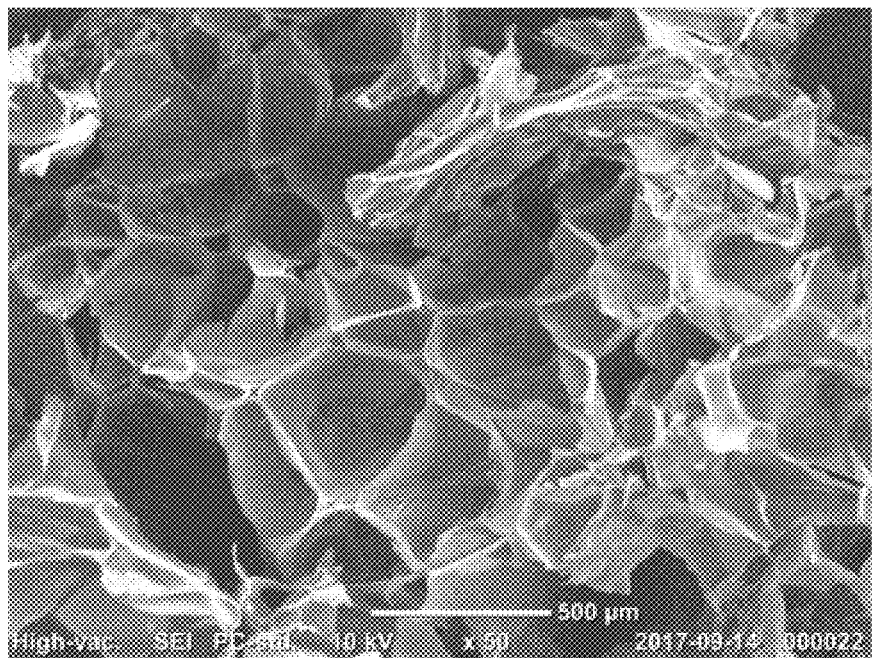

PREPARATION METHOD FOR SUPER ABSORBENT POLYMER SHEET

CROSS-REFERENCE TO RELATED APPLICATIONS

The present application is a national phase entry under 35 U.S.C. § 371 of International Application No. PCT/KR2019/005222 filed on Apr. 30, 2019, which claims priority from, Korean Patent Application No. 10-2018-0054364, filed on May 11, 2018 and Korean Patent Application No. 10-2019-0049877, filed on Apr. 29, 2019, the disclosures of which are hereby incorporated by reference in their entirety.

TECHNICAL FIELD

The present invention relates to a method of preparing a superabsorbent polymer sheet.

BACKGROUND ART

A superabsorbent polymer (SAP) is a synthetic polymeric material capable of absorbing moisture from 500 to 1000 times its own weight. Various manufacturers have called it by different names, such as SAM (Super Absorbency Material), AGM (Absorbent Gel Material), etc. Since such superabsorbent polymers started to be practically applied in sanitary products, they are no widely used not only for hygiene products such as disposable diapers for children, sanitary pads, etc., but also for water retaining soil products for gardening, water stop materials for civil engineering and construction, sheets for raising seedlings, fresh-keeping agents for food distribution fields, materials for poultices, or the like.

Generally, various hygiene products such as diapers, sanitary pads, incontinence pads, etc. include an absorbent including superabsorbent polymer particles. Such an absorbent mainly includes the superabsorbent polymer particles and fluff pulp which is used to properly fix the superabsorbent polymer particles while maintaining the shape of the absorbent and hygiene products.

However, due to the presence of the fluff pulp, it has been difficult to make the absorbent and hygiene products slim and thin, and there has been a problem in that a user feels less comfortable, because the user's skin in contact with the hygiene product gets sweaty. Moreover, since a large quantity of fluff pulp which is mainly obtained from a wood raw material is needed, there has been a backlash against its use through recent trends of environmental protection, and it has become one of the main causes of increase production costs of the absorbent layer and hygiene products.

For this reason, many attempts have been made to reduce the use of fluff pulp in the absorbent layer and hygiene products or to provide hygiene products, so-called pulpless diapers, without using fluff pulp.

Meanwhile, current superabsorbent polymers are mostly prepared and used in the form of a powder. Such superabsorbent polymers in the form of a powder may scatter or leak during preparation of sanitary materials or in actual use thereof, and they have a limited range of use because the superabsorbent polymers need to be used together with a specific type of substrate.

Accordingly, a method of preparing the superabsorbent polymer in the form of a fiber or a non-woven fabric has been suggested. However, there is no satisfactory method of obtaining a superabsorbent polymer which may have no reduction in absorption performance, may be used as a pulpless absorbent, and may exhibit sufficient flexibility, and therefore, there is still a need to study a preparation method thereof.

DISCLOSURE

Technical Problem

To solve the above problems, the present invention provides a method of preparing a superabsorbent polymer sheet having high pliability and excellent absorption performance.

Technical Solution

To solve the above problems, an aspect of the present invention provides a method of preparing a superabsorbent polymer sheet, the method including the steps of:

preparing a monomer composition by mixing an acrylic acid-based monomer having acidic groups which are at least partially neutralized, a comonomer containing poly(ethylene glycol) methyl ether (meth)acrylate, an internal crosslinking agent, an encapsulated foaming agent, an inorganic foaming agent having an average particle size of 1 µm to 100 µm, and a polymerization initiator;

forming a water-containing gel polymer by performing thermal polymerization or photopolymerization of the monomer composition; and forming the superabsorbent polymer sheet by drying the water-containing gel polymer, wherein the encapsulated foaming agent and the inorganic foaming agent are included at a weight ratio of 3:1 to 1:1.

The poly(ethylene glycol) methyl ether (meth)acrylate may be included in an amount of 5 parts by weight to 40 parts by weight with respect to 100 parts by weight of the acrylic acid-based monomer.

The encapsulated foaming agent may have an average particle size of 2 µm to 50 µm, and may have an expansion ratio of 3 times to 15 times in air.

Further, the encapsulated foaming agent may have a structure including a core which contains a hydrocarbon and a shell which surrounds the core and is formed using a thermoplastic resin.

In this regard, the hydrocarbon may be one or more selected from the group consisting of n-propane, n-butane, iso-butane, cyclobutane, n-pentane, iso-pentane, cyclopentane, n-hexane, iso-hexane, cyclohexane, n-heptane, iso-heptane, cycloheptane, n-octane, iso-octane, and cyclooctane, and the thermoplastic resin may be a polymer formed from one or more monomers selected from the group consisting of (meth)acrylate, (meth)acrylonitrile, aromatic vinyl, vinyl acetate, vinyl halide, and vinylidene halide.

The inorganic foaming agent may be one or more selected from calcium carbonate ($CaCO_3$), sodium bicarbonate ($NaHCO_3$), ammonium bicarbonate ($NH_4HCO_3$), ammonium carbonate (($NH_4)_2CO_3$), ammonium nitrite ($NH_4NO_2$), sodium borohydride ($NaBH_4$), and sodium carbonate ($Na_2CO_3$).

Preferably, an average particle size of the inorganic foaming agent may be 5 µm to 20 µm.

Preferably, the encapsulated foaming agent and the inorganic foaming agent may be included at a weight ratio of 2:1 to 1:1.

Meanwhile, the encapsulated foaming agent may be included in an amount of 0.3 to 20 parts by weight with respect to 100 parts by weight of the acrylic acid-based monomer, and the inorganic foaming agent may be included in an amount of 0.1 parts by weight or more with respect to 100 parts by weight of the acrylic acid-based monomer.

Further, the encapsulated foaming agent and the inorganic foaming agent may be included in an amount of 0.4 to 20 parts by weight with respect to 100 parts by weight of the acrylic acid-based monomer.

Effect of the Invention

A superabsorbent polymer sheet obtained by a preparation method of the present invention may be obtained in the form of a sheet or a film, unlike common superabsorbent polymers in the form of a powder, and the superabsorbent polymer sheet may be directly applied as a product, and may exhibit flexibility without concerns about scattering or leaking.

Further, the superabsorbent polymer sheet obtained by the method of preparing the superabsorbent polymer sheet of the present invention may have an open pore channel structure in which pores are connected to each other, whereby water absorption by a capillary pressure may occur to improve an absorption rate and permeability.

As such, the superabsorbent polymer may exhibit a high absorption rate as its intrinsic property while having flexibility and pliability, and thus it may be applied to a variety of products which are required to have pliability and high absorbency.

Further, the superabsorbent polymer sheet may be used as a pulpless absorbent.

BRIEF DESCRIPTION OF DRAWING

FIG. 1 is a scanning electron microscopy (SEM) image showing a cross-section of a superabsorbent polymer sheet prepared according to one embodiment of the present invention.

BEST MODE FOR CARRYING OUT THE INVENTION

While the present invention is susceptible to various modifications and alternative forms, specific embodiments will be illustrated and described in detail as follows. It should be understood, however, that the description is not intended to limit the present invention to the particular forms disclosed, but on the contrary, the intention is to cover all modifications, equivalents, and alternatives falling within the spirit and scope of the invention.

As used herein, Dn which is a particle diameter of a particle represents a particle diameter at the n vol % point in the cumulative distribution of particles according to the particle diameter. That is, D50 is a particle diameter at the 50% point in the cumulative distribution of particles when particle diameters of particles are accumulated in ascending order, D90 is a particle diameter at the 90% point in the cumulative distribution of particles according to the particle diameter, and D10 is a particle diameter at the 10% point in the cumulative distribution of particles according to the particle diameter. As used herein, the average particle diameter means the D50 particle diameter. Dn may be determined using a laser diffraction method. In detail, the particle diameter Dn may be determined by dispersing a powder to be measured in a dispersion medium, which is then introduced into a commercially available laser diffraction particle size analyzer (e.g., Mastersizer 3000), measuring a difference in diffraction patterns according to the particle size when a laser beam passes through particles, and then calculating a particle size distribution.

Hereinafter, a method of preparing a superabsorbent polymer sheet according to one embodiment of the present invention will be described.

According to one embodiment of the present invention, a method of preparing a superabsorbent polymer sheet is provided, the method including the steps of: preparing a monomer composition by mixing an acrylic acid-based monomer having acidic groups which are at least partially neutralized, a comonomer containing poly(ethylene glycol) methyl ether (meth)acrylate, an internal crosslinking agent, an encapsulated foaming agent, an inorganic foaming agent having an average particle diameter (D50) of 1 µm to 100 µm, and a polymerization initiator; forming a water-containing gel polymer by performing thermal polymerization or photopolymerization of the monomer composition; and forming the superabsorbent polymer sheet by drying the water-containing gel polymer, wherein the encapsulated foaming agent and the inorganic foaming agent are included at a weight ratio of 3:1 to 1:1.

In the preparation method of the present invention, the monomer composition which is a raw material of the superabsorbent polymer may include an acrylic acid-based monomer having acidic groups which are at least partially neutralized, a comonomer containing poly(ethylene glycol) methyl ether (meth)acrylate, an internal crosslinking agent, an encapsulated foaming agent, an inorganic foaming agent having an average particle diameter (D50) of 1 µm to 100 µm, and a polymerization initiator.

First, the acrylic acid-based monomer is a compound represented by the following Chemical Formula 1:

$$R^1\text{—COOM}^1 \qquad \text{[Chemical Formula 1]}$$

in Chemical Formula 1, $R^1$ is an alkyl group containing an unsaturated bond and having 2 to 5 carbon atoms, and $M^1$ is a hydrogen atom, a monovalent or divalent metal, an ammonium group, or an organic amine salt.

Preferably, the acrylic acid-based monomer may include one or more selected from the group consisting of acrylic acid, methacrylic acid, and a monovalent metal salt thereof, a divalent metal salt thereof, an ammonium salt thereof, and an organic amine salt thereof.

Here, the acrylic acid-based monomer may have acidic groups which are at least partially neutralized. Preferably, those partially neutralized with an alkali substance such as sodium hydroxide, potassium hydroxide, ammonium hydroxide, etc. may be used as the monomer. In this regard, a degree of neutralization of the acrylic acid-based monomer may be 40 mol % to 95 mol %, or 40 mol % to 80 mol %, or 45 mol % to 75 mol %. The range of the neutralization degree may vary depending on final physical properties. However, an excessively high degree of neutralization renders the neutralized monomers precipitated, and thus polymerization may not occur readily, whereas an excessively low degree of neutralization not only greatly deteriorates absorbency of the polymer, but also endows the polymer with hard-to-handle properties, such as of elastic rubber.

A concentration of the acrylic acid-based monomer may be about 20% by weight to about 60% by weight, preferably about 40% by weight to about 50% by weight, with respect to the monomer composition including the raw materials of the superabsorbent polymer and a solvent, and the concentration may be properly controlled, taking into consideration a polymerization time and reaction conditions. However, if the monomer concentration is too low, the yield of the superabsorbent polymer may become low and an economic problem may occur. On the contrary, if the concentration is too high, there is a process problem that a part of the monomers is precipitated, or pulverization efficiency is lowered upon pulverization of the polymerized water-containing gel polymer, and the physical properties of the superabsorbent polymer may be reduced.

The monomer composition of the present invention may include poly(ethylene glycol) methyl ether (meth)acrylate as a comonomer.

The poly(ethylene glycol) methyl ether (meth)acrylate may be copolymerized together with the acrylic acid-based monomer during the polymerization process, which allows polymerization of a superabsorbent polymer having a polymer structure with flexibility.

To form an optimized polymer structure, a repeating unit of ethylene glycol in the poly(ethylene glycol) methyl ether (meth)acrylate may be 3 to 100, 3 to 80, or 3 to 50.

A content of the poly(ethylene glycol) methyl ether (meth)acrylate may be 5 parts by weight to 40 parts by weight, preferably 5 parts by weight to 30 parts by weight, or more preferably 10 parts by weight to 30 parts by weight, with respect to 100 parts by weight of the acrylic acid-based monomer. If the content of the comonomer is too low, the effect of improving flexibility may not be obtained. If the content is too high, an absorption rate and absorbency may be reduced. From this point of view, the above content range may be preferred.

In the present invention, the internal crosslinking agent may be, for example, poly(meth)acrylate-based compounds of polyols, e.g., poly(meth)acrylate-based compounds of polyols having 2 to 10 carbon atoms. More specific examples thereof may include trimethylolpropane tri(meth)acrylate, ethylene glycol di(meth)acrylate, poly(ethylene glycol) di(meth)acrylate, propylene glycol di(meth)acrylate, poly(propylene glycol) di(meth)acrylate, butanedioldi(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentacrylate, glycerin tri(meth)acrylate, or pentaerythritol tetraacrylate, and preferably, poly(ethylene glycol) diacrylate.

The internal crosslinking agent may be included at a concentration of about 0.01% by weight to about 2% by weight, or 0.1% by weight to 0.5% by weight with respect to the monomer composition, thereby crosslinking the polymerized polymer.

The monomer composition of the present invention may include a foaming agent. In this regard, it may include an encapsulated foaming agent and an inorganic foaming agent having an average particle diameter (D50) of 1 µm to 100 µm at the same time. When the two kinds of the foaming agents are used in a mixture, there are effects of obtaining high porosity and open pores of the superabsorbent polymer sheet. In other words, when the encapsulated foaming agent and the inorganic foaming agent are used at the same time, as in the present invention, main pores having a size suitable for securing high porosity inside the superabsorbent polymer sheet are generated by the encapsulated foaming agent, and a micropore channel is formed between the main pores by the inorganic foaming agent to secure an open pore channel structure in which main pores are connected to each other. Therefore, due to the micropore channel structure, rapid absorption of water by capillary pressure may occur, and the superabsorbent polymer to be prepared may exhibit excellent centrifuge retention capacity and absorbency under pressure, as compared with those prepared by using each of the foaming agents alone.

The encapsulated foaming agent may exist in an encapsulated state during polymerization of the monomer composition and may expand by heat, and may be foamed by high-temperature heat which is applied during a drying process described below. As a result, pores having a proper size are generated between polymer structures of the superabsorbent polymer, and thus the superabsorbent polymer sheet may exhibit the open pore channel structure.

The encapsulated foaming agent may have a structure including a core which contains hydrocarbons and a shell which surrounds the core and is formed using a thermoplastic resin. Such an encapsulated foaming agent may have expansion properties which may vary depending on components constituting the core and the shell, weights of the respective components, and average particle sizes thereof. By adjusting these factors, it is possible to expand pores to a desired size and to control porosity of the superabsorbent polymer sheet.

Meanwhile, in order to examine whether pores with a desired size are generated, it is necessary to examine expansion properties of the encapsulated foaming agent. However, the foamed shape of the encapsulated foaming agent inside the superabsorbent polymer is difficult to define as one shape, because it may vary depending on the preparation conditions of the superabsorbent polymer. Therefore, the encapsulated foaming agent is first foamed in air, and then its expansion ratio and size are examined, thereby determining whether it is suitable for forming desired pores.

In detail, the encapsulated foaming agent is applied on a glass petri dish, which is then heated in air at 180° C. for 5 minutes to expand the encapsulated foaming agent. In this regard, when the encapsulated foaming agent exhibits a maximum expansion ratio of 3 times to 15 times, 5 times to 15 times, or 8.5 times to 10 times in air, it may be determined as being suitable for forming an appropriate open pore structure in the method of preparing the superabsorbent polymer sheet of the present invention.

The encapsulated foaming agent may have an average particle diameter, i.e., a D50 particle diameter, of 5 µm to 50 µm, 5 µm to 30 µm, 5 µm to 20 µm, or 7 µm to 17 µm. When the encapsulated foaming agent exhibits the above average particle diameter, it may be determined as being suitable for achieving appropriate porosity.

Further, when the encapsulated foaming agent exhibits a maximum expansion diameter of 20 µm to 190 µm, 50 µm to 190 µm, 70 µm to 190 µm, or µm 75 to 190 µm in air, it may be determined as being suitable for forming an appropriate open pore structure in the method of preparing the superabsorbent polymer sheet of the present invention.

Further, the maximum expansion ratio and the maximum expansion diameter of the encapsulated foaming agent may be measured by analyzing the shapes of pores generated in the prepared superabsorbent polymer sheet using scanning electron microscopy (SEM).

The hydrocarbon constituting the core of the encapsulated foaming agent may be one or more selected from the group consisting of n-propane, n-butane, iso-butane, cyclobutane, n-pentane, iso-pentane, cyclopentane, n-hexane, iso-hexane, cyclohexane, n-heptane, iso-heptane, cycloheptane, n-octane, iso-octane, and cyclooctane. Among them, hydrocarbons having 3 to 5 carbon atoms (n-propane, n-butane, iso-butane, cyclobutane, n-pentane, iso-pentane, and cyclopentane) may be suitable for forming the pores having the above-described size, and iso-butane may be the most suitable.

The thermoplastic resin constituting the shell of the encapsulated foaming agent may be a polymer formed from one or more monomers selected from the group consisting of (meth)acrylate, (meth)acrylonitrile, aromatic vinyl, vinyl acetate, vinyl halide, and vinylidene halide. Among them, a copolymer of (meth)acrylate and (meth)acrylonitrile may be the most suitable for forming the pores having the above-described size.

The encapsulated foaming agent may include the hydrocarbon in an amount of 10% by weight to 30% by weight with respect to the total weight of the encapsulated foaming agent. This range may be the most suitable for forming the open pore structure.

A directly prepared encapsulated foaming agent may be used, or a commercially available foaming agent satisfying the above-described conditions may be used.

Further, the encapsulated foaming agent may be used in an amount of 0.3 to 20 parts by weight, preferably 0.5 to 10 parts by weight, and more preferably 1 to 10 parts by weight with respect to 100 parts by weight of the acrylic acid-based monomer. If the content of the encapsulated foaming agent is too low, the open pore structure may not be properly formed, and appropriate porosity may not be secured. If the content of the encapsulated foaming agent is too high, the porosity becomes too high, and as a result, strength of the superabsorbent polymer may be weakened. From this point of view, the above content range may be preferred.

The inorganic foaming agent may preferably have an average particle diameter, i.e., a D50 particle diameter, of 1 μm to 100 μm, and more preferably 3 μm to 50 μm, or 5 μm to 20 μm. Such a micro-sized inorganic foaming agent may function as a foaming agent, and at the same time, as an inorganic support which imparts mechanical strength to the superabsorbent polymer sheet. If the average particle diameter of the inorganic foaming agent is less than 1 μm, open pores may be generated with high porosity due to many nucleation sites, but its function as the inorganic support may be weak, and thus it is difficult to secure strength of the superabsorbent polymer sheet. On the contrary, if the average particle diameter of the inorganic foaming agent is more than 100 μm, the inorganic foaming agent may not properly function as the foaming agent for forming micropores, and may serve only as the inorganic support. Therefore, to prepare the superabsorbent sheet having open pores and appropriate strength, particles within the above range may be preferably used.

As the inorganic foaming agent, any foaming agent commonly known may be used without limitation. Specifically, one or more selected from the group consisting of calcium carbonate ($CaCO_3$), sodium bicarbonate ($NaHCO_3$), ammonium bicarbonate ($NH_4HCO_3$), ammonium carbonate (($NH_4)_2CO_3$), ammonium nitrite ($NH_4NO_2$), sodium borohydride ($NaBH_4$), and sodium carbonate ($Na_2CO_3$) may be used. Among them, calcium carbonate and/or sodium carbonate may be preferably used, taking into consideration stability in a neutralization solution.

The inorganic foaming agent may be used in an amount of 0.1 parts by weight or more, preferably 0.2 to 10 parts by weight, and more preferably 0.3 to 5 parts by weight, with respect to 100 parts by weight of the acrylic acid-based monomer. If the content of the inorganic foaming agent is too low, there is a problem in that closed pores may be generated. If the content of the inorganic foaming agent is too high, there is a problem in that mechanical strength may be reduced due to high porosity.

A mixing ratio of the encapsulated foaming agent and the inorganic foaming agent may be preferably a weight ratio of 3:1 to 1:1, and more preferably, a weight ratio of 2:1 to 1:1. Within this range, high porosity and improvement of mechanical strength may be obtained, thereby improving centrifuge retention capacity and absorbency under pressure of the superabsorbent polymer sheet to be prepared.

Further, the encapsulated foaming agent and the inorganic foaming agent may be included in an amount of 20 parts by weight or less, and more preferably, 0.4 to 20 parts by weight, 0.7 to 10 parts by weight, or 1 to 5 parts by weight with respect to 100 parts by weight of the acrylic acid monomer. If the total amount of the foaming agents is too large, the degree of foaming is too high, and thus the strength of the superabsorbent polymer may be reduced. If the total amount of the foaming agents is too small, the open pore structure is hardly formed. Therefore, it is preferable that the total amount thereof satisfies the above range.

In the method of preparing the superabsorbent polymer sheet of the present invention, the polymerization initiator used during polymerization is not particularly limited, as long as it is generally used in the preparation of the superabsorbent polymer.

Specifically, the polymerization initiator may be a thermal polymerization initiator or a photo-polymerization initiator by UV irradiation, depending on a polymerization method. However, even though the photopolymerization is performed, a certain amount of heat may be generated by UV irradiation or the like, and is also generated with the exothermic polymerization reaction. Therefore, the thermal polymerization initiator may be further included.

As the photo-polymerization initiator, a compound capable of forming radicals by light such as UV may be used without limitations in the constitution.

For example, one or more selected from the group consisting of benzoin ether, dialkyl acetophenone, hydroxyl alkylketone, phenyl glyoxylate, benzyl dimethyl ketal, acyl phosphine, and α-aminoketone may be used as the photo-polymerization initiator. Meanwhile, as a specific example of the acyl phosphine, commercially available lucirin TPO, namely, 2,4,6-trimethyl-benzoyl-trimethyl phosphine oxide, may be used. More various photo-polymerization initiators are well disclosed in "UV Coatings: Basics, Recent Developments and New Application (Elsevier 2007)" written by Reinhold Schwalm, p 115, however, they are not limited to the above-described examples.

The photo-polymerization initiator may be included in an amount of about 0.01% by weight to about 1.0% by weight in the monomer composition. If the concentration of the photo-polymerization initiator is too low, the polymerization rate may become low. If the concentration of the photo-polymerization initiator is too high, the molecular weight of the superabsorbent polymer may become low and its physical properties may not be uniform.

Further, one or more selected from the group consisting of persulfate-based initiators, azo-based initiators, hydrogen peroxide, and ascorbic acid may be used as the thermal polymerization initiator. Specific examples of the persulfate-based initiators may include sodium persulfate ($Na_2S_2O_8$), potassium persulfate ($K_2S_2O_8$), ammonium persulfate (($NH_4)_2S_2O_8$), or the like. Examples of the azo-based initiators may include 2,2-azobis(2-amidinopropane)dihydrochloride, 2,2-azobis-(N,N-dimethylene)isobutyramidine dihydrochloride, 2-(carbamoylazo)isobutylonitril, 2,2-azobis(2-[2-imidazolin-2-yl]propane)dihydrochloride, 4,4-azobis-(4-cyanovaleric acid), or the like. More various thermal polymerization initiators are well-disclosed in 'Principle of Polymerization (Wiley, 1981)' written by Odian, p 203, however, they are not limited to the above-described examples.

The thermal polymerization initiator may be included in an amount of about 0.001% by weight to about 0.5% by weight in the monomer composition. If the concentration of the thermal polymerization initiator is too low, additional thermal polymerization hardly occurs, and thus the sufficient addition effect of the thermal polymerization initiator may not be obtained. If the concentration of the thermal polymerization initiator is too high, the molecular weight of the superabsorbent polymer may become low and its physical properties may not be uniform.

In the preparation method of the present invention, the monomer composition may further include an additive such as a thickener, a plasticizer, a preservation stabilizer, an antioxidant, etc., if necessary.

The raw materials such as the above-described acrylic acid-based unsaturated monomer, comonomer, internal crosslinking agent, polymerization initiator, and additive may be prepared in the form of a solution in which the monomer composition is dissolved in a solvent. The solvent may be included in a residual amount excluding the above-described components from the total weight of the monomer composition.

As the solvent to be applicable, any solvent may be used without limitations in the constitution as long as it is able to dissolve the above components, and for example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, and N,N-dimethylacetamide may be used in combination.

Next, the water-containing gel polymer may be formed by thermal polymerization or photo-polymerization of the monomer composition.

The method of forming the water-containing gel polymer by thermal polymerization or photo-polymerization of the monomer composition is not particularly limited in the constitution, as long as it is a polymerization method generally used in the art related to the preparation of the superabsorbent polymer.

Specifically, the polymerization method is largely classified into the thermal polymerization and the photo-polymerization according to a polymerization energy source. The thermal polymerization may be commonly carried out in a reactor like a kneader equipped with agitating spindles, whereas the photo-polymerization may be carried out in a reactor equipped with a movable conveyor belt. The above-described polymerization method is only an example, and the present invention is not limited to the above-described polymerization method.

A reaction temperature of the thermal polymerization or photopolymerization of the monomer composition is not particularly limited, but the reaction temperature may be, for example, 80° C. to 120° C., preferably 90° C. to 110° C.

In this regard, the water-containing gel polymer thus obtained by the method may generally have a water content of about 40% by weight to about 80% by weight. Further, the term "water content", as used herein, means a water content in the total weight of the water-containing gel polymer, which is obtained by subtracting the weight of the dry polymer from the weight of the water-containing gel polymer. Specifically, the water content is defined as a value calculated by measuring the weight loss according to evaporation of water in the polymer during the drying process of increasing the temperature of the polymer with infrared heating. In this regard, the water content is measured under the drying conditions which are determined as follows: the temperature is increased from room temperature to about 180° C. and then the temperature is maintained at 180° C., and the total drying time is determined as 20 minutes, including 5 minutes for the temperature rising step.

Next, the water-containing gel polymer is molded in the form of a sheet, and dried to form the superabsorbent polymer sheet.

In this regard, the drying temperature of the drying step may be about 120° C. to about 250° C. When the drying temperature is lower than 120° C., there is a concern about excessively extended drying time or deterioration of the physical properties of the superabsorbent polymer finally formed, and when the drying temperature is higher than 250° C., only the surface of the polymer is dried, and thus there is a concern about deterioration of the physical properties of the superabsorbent polymer finally formed. Therefore, the drying may be preferably performed at a temperature of about 120° C. to about 250° C., and more preferably about 140° C. to about 200° C. In this drying step, the foaming agent may be foamed to form the micropore channels between main pores, thereby obtaining the open pore channel structure.

Meanwhile, the drying may be carried out for about 20 minutes to about 90 minutes, taking into consideration the process efficiency, but is not limited thereto.

Any drying method may be selected and used in the drying step without limitation in the constitution, as long as it is commonly used in the drying process of the water-containing gel polymer. Specifically, the drying step may be carried out by a method of supplying hot air, irradiating infrared rays, irradiating microwaves, irradiating ultraviolet rays, or the like.

When the drying step as above is finished, the water content of the superabsorbent polymer sheet may be about 10% by weight or more, for example, about 10% by weight to about 40% by weight, or about 15% by weight to about 30% by weight. When the water content of the superabsorbent polymer sheet is within the above range, it is possible to secure flexibility of the sheet.

According to one embodiment of the present invention, the superabsorbent polymer sheet obtained by the above processes may have a thickness of about 100 µm or more, or 1000 µm, or 5000 µm and about 10 cm or less, or about 5 cm or less, or about 1 cm or less. If the thickness of the superabsorbent polymer sheet is too thin, the sheet may be torn due to its low strength. If the thickness of the superabsorbent polymer sheet is too thick, drying and processing may be difficult. From this point of view, the superabsorbent polymer sheet may preferably have a thickness within the above range.

According to the method of preparing the superabsorbent polymer sheet of the present invention, the superabsorbent polymer sheet may be in the form of a sheet in which at least some of the pores may be connected to each other to form the open pore channel structure, and therefore, water absorption by a capillary pressure may occur, thereby improving the absorption rate and permeability and providing the superabsorbent polymer sheet itself as a pulpless absorbent.

The superabsorbent polymer sheet prepared according to the present invention may have the open pore channel structure in which at least some of pores are connected to each other, and due to the open pore channel structure, the superabsorbent polymer sheet may absorb water by a capillary pressure. Accordingly, the superabsorbent polymer sheet may have an improved absorption rate and permeability, as compared with known superabsorbent polymers in the form of powder.

Further, the superabsorbent polymer sheet may have centrifuge retention capacity (CRC) in the range of about 10 g/g to about 40 g/g, preferably about 15 g/g to about 40 g/g, and more preferably about 25 g/g to about 40 g/g, as measured in accordance with the EDANA method WSP 241.2.

In addition, the superabsorbent polymer sheet may have absorbency under pressure (AUP) of 0.7 psi in the range of about 5 g/g to about 20 g/g, preferably about 7 g/g to about 15 g/g, and more preferably about 10 g/g to about 15 g/g, as measured in accordance with the EDANA method WSP 242.2.

As described above, the superabsorbent polymer sheet of the present invention may have excellent absorption properties and permeability, thereby being used as a pulpless absorbent.

Hereinafter, the actions and effects of the present invention will be described in more detail with reference to the specific examples. However, these examples are for illustrative purposes only, and the scope of the present invention is not intended to be limited thereby.

EXAMPLES

In the following examples, particle diameters of an encapsulated foaming agent and an inorganic foaming agent were measured using a laser diffraction method. In detail, 1 mg of powder to be measured was dispersed in 30 g of distilled water, and then introduced into a laser diffraction particle size analyzer (Mastersizer 3000). When a laser beam passed through particles, a difference in diffraction patterns according to the particle size was measured to calculate a particle size distribution. D50 was determined by calculating a particle diameter at the 50% point in the cumulative distribution of particles according to the particle diameter in the analyzer.

Preparation of Superabsorbent Polymer Sheet

Example 1

27.5 g of acrylic acid, 35.7 g of caustic soda (NaOH, 30 wt % solution), and 5.7 g of water were mixed to prepare a neutralization solution (a solid content: 50% by weight) in which about 70 mol % of the acrylic acid was neutralized.

To the neutralization solution, 5.5 g of poly(ethylene glycol) methyl ether (meth)acrylate (product name: FA-401, manufacturer: HanNong Chemicals Inc.) as a comonomer, 0.08 g of poly(ethylene glycol) diacrylate (MW=330, manufacturer: aldrich), 0.06 g of sodium persulfate, 0.41 g of an encapsulated foaming agent (Akzonobel, Expancel 031 DU 40, average particle diameter (D50): 16 μm), and 0.41 g of calcium carbonate ($CaCO_3$) (average particle diameter (D50): 12 μm) as an inorganic foaming agent were added to prepare a monomer composition.

The monomer composition was subjected to high-shear mixing using a mechanical mixer at a speed of 500 rpm for about 10 minutes.

Thereafter, the monomer composition was introduced into a polymerization reactor though a feed section, and polymerization was allowed to prepare a water-containing gel polymer. At this time, the polymerization reactor was maintained at a temperature of 100° C., and a maximum temperature of the polymerization was 110° C. and a polymerization time was 10 minutes.

Subsequently, the water-containing gel polymer was dried at 180° C. for 5 minutes, and was cut using a cutting machine in the form of a sheet (thickness: about 2 mm).

Example 2

A superabsorbent polymer sheet was prepared in the same manner as in Example 1, except that the encapsulated foaming agent and the calcium carbonate foaming agent were used in an amount of 0.75% by weight, respectively, with respect to 100% by weight of acrylic acid in Example 1.

Example 3

A superabsorbent polymer sheet was prepared in the same manner as in Example 1, except that the encapsulated foaming agent and the calcium carbonate foaming agent were used in an amount of 1.5% by weight and 0.75% by weight, respectively, with respect to 100% by weight of acrylic acid in Example 1.

Example 4

A superabsorbent polymer sheet was prepared in the same manner as in Example 1, except that the encapsulated foaming agent and the sodium carbonate ($Na_2CO_3$) foaming agent (average particle diameter (D50): 12 μm) were used in an amount of 0.75% by weight, respectively, with respect to 100% by weight of acrylic acid in Example 1.

Comparative Example 1

A superabsorbent polymer sheet was prepared in the same manner as in Example 1, except that no calcium carbonate foaming agent was used in Example 1.

Comparative Example 2

A superabsorbent polymer sheet was prepared in the same manner as in Example 1, except that no encapsulated foaming agent was used in Example 1.

Comparative Example 3

A superabsorbent polymer sheet was prepared in the same manner as in Example 1, except that no encapsulated foaming agent and no calcium carbonate foaming agent were used in Example 1.

Comparative Example 4

A superabsorbent polymer sheet was prepared in the same manner as in Example 1, except that the encapsulated foaming agent and the calcium carbonate foaming agent were used in an amount of 4.5% by weight and 1.5% by weight, respectively, with respect to 100% by weight of acrylic acid in Example 1.

Comparative Example 5

A superabsorbent polymer sheet was prepared in the same manner as in Example 1, except that the encapsulated foaming agent and the calcium carbonate foaming agent were used in an amount of 1.5% by weight and 3.0% by weight, respectively, with respect to 100% by weight of acrylic acid in Example 1.

Experimental Example

Characterization of Superabsorbent Polymer Sheet
(1) Cross-Section of Superabsorbent Polymer Sheet
An image of scanning electron microscopy (SEM) showing a cross-section of the superabsorbent polymer sheet prepared according to Example 1 of the present invention is shown in FIG. 1. Referring to FIG. 1, it was observed that an open pore channel structure was formed on the surface of the superabsorbent polymer sheet prepared according to Example 1 of the present invention
(2) Measurement of Centrifuge Retention Capacity (CRC) and Absorbency Under Pressure (AUP)
Centrifuge retention capacity (CRC) and absorbency under pressure (AUP) of 0.7 psi were measured for the superabsorbent polymer sheets of the examples and comparative examples in accordance with the EDANA method WSP 241.2 and the EDANA method WSP 242.2, respectively. The results are shown in Table 1 below.

TABLE 1

|  | Example 1 | Example 2 | Example 3 | Example 4 | Comparative Example 1 | Comparative Example 2 | Comparative Example 3 | Comparative Example 4 | Comparative Example 5 |
|---|---|---|---|---|---|---|---|---|---|
| Encapsulated foaming agent[1] | 1.5% | 0.75% | 1.5% | 0.75% | 1.5% | — | — | 4.5% | 1.5% |
| Inorganic foaming agent[1] | 1.5% | 0.75% | 0.75% | 0.75% | — | 1.5% | — | 1.0% | 3.0% |
| CRC (g/g) | 28.9 | 27.1 | 27.9 | 24.1 | 21.2 | 21.8 | 20.9 | 18.2 | 22.9 |
| AUP (g/g) | 10.4 | 11.3 | 10.3 | 10.5 | 11.0 | 7.9 | 7.3 | 8.0 | 9.7 |

[1]% by weight of foaming agent with respect to 100 % by weight of acrylic

Referring to Table 1, it was confirmed that the superabsorbent polymer sheets which were prepared by using the encapsulated foaming agent and the inorganic foaming agent at a weight ratio of 3:1 to 1:1 at the same time showed excellent centrifuge retention capacity and absorbency under pressure, as compared with superabsorbent polymer sheets prepared by using each of the foaming agents alone or by using no foaming agents. In contrast, Comparative Example 4 and Comparative Example 5 prepared by using the encapsulated foaming agent and the inorganic foaming agent at a weight ratio of more than 3:1 and at a weight ratio of less than 1:1, respectively showed remarkably low centrifuge retention capacity and absorbency under pressure, as compared with the examples. These results indicate that, in order to obtain excellent physical properties due to the open pore structure of the superabsorbent polymer sheet, the encapsulated foaming agent and the inorganic foaming agent are required to satisfy the weight ratio of the present invention.

The invention claimed is:
1. A method of preparing a superabsorbent polymer sheet, comprising:
   preparing a monomer composition by mixing an acrylic acid-based monomer having acidic groups which are at least partially neutralized, a comonomer including poly(ethylene glycol) methyl ether (meth)acrylate, an internal crosslinking agent, an encapsulated foaming agent, an inorganic foaming agent having an average particle diameter of 1 μm to 100 μm, and a polymerization initiator;
   forming a water-containing gel polymer by performing thermal polymerization or photopolymerization of the monomer composition; and
   forming the superabsorbent polymer sheet by drying the water-containing gel polymer,
   wherein the encapsulated foaming agent and the inorganic foaming agent are included at a weight ratio of 3:1 to 1:1.
2. The method of claim 1, wherein the poly(ethylene glycol) methyl ether (meth)acrylate is included in an amount of 5 parts by weight to 40 parts by weight with respect to 100 parts by weight of the acrylic acid-based monomer.
3. The method of claim 1, wherein the encapsulated foaming agent has an average particle diameter of 2 μm to 50 μm.
4. The method of claim 1, wherein the encapsulated foaming agent has an expansion ratio of 3 times to 15 times in air.
5. The method of claim 1, wherein the encapsulated foaming agent has a structure including a core which contains a hydrocarbon and a shell which surrounds the core and is formed using a thermoplastic resin.
6. The method of claim 5, wherein the hydrocarbon is one or more selected from the group consisting of n-propane, n-butane, iso-butane, cyclobutane, n-pentane, iso-pentane, cyclopentane, n-hexane, iso-hexane, cyclohexane, n-heptane, iso-heptane, cycloheptane, n-octane, iso-octane, and cyclooctane.
7. The method of claim 5, wherein the thermoplastic resin is a polymer formed from one or more monomers selected from the group consisting of (meth)acrylate, (meth)acrylonitrile, aromatic vinyl, vinyl acetate, vinyl halide, and vinylidene halide.
8. The method of claim 1, wherein the inorganic foaming agent is one or more selected from the group consisting of calcium carbonate ($CaCO_3$), sodium bicarbonate ($NaHCO_3$), ammonium bicarbonate ($NH_4HCO_3$), ammonium carbonate (($NH_4)_2CO_3$), ammonium nitrite ($NH_4NO_2$), sodium borohydride ($NaBH_4$), and sodium carbonate ($Na_2CO_3$).
9. The method of claim 1, wherein the inorganic foaming agent has an average particle diameter of 5 μm to 20 μm.
10. The method of claim 1, wherein the encapsulated foaming agent and the inorganic foaming agent are included at a weight ratio of 2:1 to 1:1.
11. The method of claim 1, wherein the encapsulated foaming agent is included in an amount of 0.3 to 20 parts by weight with respect to 100 parts by weight of the acrylic acid-based monomer.
12. The method of claim 1, wherein the inorganic foaming agent is included in an amount of 0.1 parts by weight or more with respect to 100 parts by weight of the acrylic acid-based monomer.

13. The method of claim 1, wherein the encapsulated foaming agent and the inorganic foaming agent are included in a total amount of 0.4 to 20 parts by weight with respect to 100 parts by weight of the acrylic acid-based monomer.

\* \* \* \* \*